(12) United States Patent
Ritter et al.

(10) Patent No.: US 8,530,819 B2
(45) Date of Patent: Sep. 10, 2013

(54) DIRECT CURRENT (DC) CORRECTION CIRCUIT FOR A TIME OF FLIGHT (TOF) PHOTODIODE FRONT END

(75) Inventors: David W. Ritter, San Jose, CA (US); Philip Golden, Menlo Park, CA (US); Carl Warren Craddock, San Francisco, CA (US); Kevin Brehmer, Redwood Shores, CA (US)

(73) Assignee: Intersil Americas Inc., Milpitas, CA (US)

( * ) Notice: Subject to any disclaimer, the term of this patent is extended or adjusted under 35 U.S.C. 154(b) by 353 days.

(21) Appl. No.: 13/013,146

(22) Filed: Jan. 25, 2011

(65) Prior Publication Data

US 2011/0181254 A1    Jul. 28, 2011

Related U.S. Application Data

(60) Provisional application No. 61/298,895, filed on Jan. 27, 2010.

(51) Int. Cl.
 *G05F 1/10* (2006.01)
(52) U.S. Cl.
 USPC ............. 250/214 A; 250/208.1; 330/308
(58) Field of Classification Search
 USPC ............. 250/214 B, 221, 214 AL, 214 C, 250/214 R; 340/331
 See application file for complete search history.

(56) References Cited

U.S. PATENT DOCUMENTS

| | | | |
|---|---|---|---|
| 3,996,590 A | 12/1976 | Hammack | |
| 4,458,212 A | 7/1984 | Brehmer et al. | |
| 4,542,475 A | 9/1985 | Acampora | |
| 4,551,710 A | 11/1985 | Troup et al. | |
| 4,648,364 A | 3/1987 | Wills | |
| 4,942,561 A | 7/1990 | Ohishi et al. | |
| 5,055,671 A | 10/1991 | Jones | |
| 5,563,701 A | 10/1996 | Cho | |
| 5,593,430 A | 1/1997 | Renger | |
| 5,828,899 A | 10/1998 | Richard et al. | |
| 5,892,540 A | 4/1999 | Kozlowski et al. | |
| 6,111,256 A | 8/2000 | Shpater | |
| 6,392,539 B1 | 5/2002 | Kanasugi | |
| 6,462,726 B1 | 10/2002 | Hamada et al. | |

(Continued)

FOREIGN PATENT DOCUMENTS

WO    8704034 A1    7/1987
WO    2009088662 A2    7/2009

OTHER PUBLICATIONS

International Search Report and Written Opinion, mailing dated Mar. 25, 2011, for International Application No. PCT/US11/22644, 8 pages.

(Continued)

*Primary Examiner* — Tony Ko
(74) *Attorney, Agent, or Firm* — Vierra Magen Marcus LLP

(57) ABSTRACT

A system and method that compensates for the effects of ambient light in a time of flight (TOF) sensor front end is provided. Moreover, a direct current (DC) correction loop is utilized at the front end, which removes a DC component from a current generated by the TOF sensor and accordingly prevents saturating the front end. The DC correction loop attenuates the DC component without adding significant thermal noise at a modulation frequency and provides a corrected signal to the front end circuitry. The corrected signal is processed and utilized to detect a position of an object within the optical field of the sensor.

18 Claims, 8 Drawing Sheets

(56) References Cited

U.S. PATENT DOCUMENTS

| | | | |
|---|---|---|---|
| 6,744,248 B2 | 6/2004 | Buchhold et al. | |
| 6,753,950 B2 | 6/2004 | Morcom | |
| 6,803,555 B1 * | 10/2004 | Parrish et al. | 250/214 C |
| 6,819,782 B1 | 11/2004 | Imagawa et al. | |
| 6,836,212 B2 | 12/2004 | Sawinski | |
| 6,888,938 B2 | 5/2005 | Cui et al. | |
| 7,212,655 B2 | 5/2007 | Tumey et al. | |
| 7,486,386 B1 | 2/2009 | Holcombe et al. | |
| 7,532,870 B2 | 5/2009 | Ling | |
| 7,616,032 B2 | 11/2009 | Jang | |
| 7,619,293 B2 | 11/2009 | Hasegawa | |
| 7,620,202 B2 | 11/2009 | Fujimura et al. | |
| 7,642,501 B1 * | 1/2010 | Fassbender et al. | 250/214 A |
| 7,714,268 B2 * | 5/2010 | Leijssen et al. | 250/214 R |
| 2002/0097743 A1 | 7/2002 | Baydar et al. | |
| 2003/0234341 A1 | 12/2003 | Osborn | |
| 2006/0120621 A1 | 6/2006 | Larkin et al. | |
| 2007/0013791 A1 | 1/2007 | Kinoshita et al. | |
| 2007/0121095 A1 | 5/2007 | Lewis | |
| 2008/0119716 A1 | 5/2008 | Boric-Lubecke et al. | |
| 2008/0205820 A1 | 8/2008 | Zheng et al. | |
| 2008/0266128 A1 | 10/2008 | Leone et al. | |
| 2009/0006730 A1 | 1/2009 | Gara et al. | |
| 2009/0027529 A1 | 1/2009 | Jung et al. | |
| 2009/0295729 A1 | 12/2009 | Kuo et al. | |

OTHER PUBLICATIONS

Ryan, et al., "A long-range, widefield-of-view, infrared eyeblink detector". Journal of Neuroscience Methods 152 (2006) 74-82, Apr. 2006, abstract: Fig 3, 4: pp. 79, col. 2.

International Search Report and Written Opinion, mailing date Mar. 21, 2011, for International Application No. PCT/US11/022646, 14 pages.

International Search Report and Written Opinion, mailing date Apr. 6, 2011, for International Application No. PCT/US2011/022647, 17 pages.

International Search Report and Written Opinion, mailing date Mar. 28, 2011, for International Application No. PCT/US2011/022649, 13 pages.

International Search Report and Written Opinion, mailing date Mar. 28, 2011, for International Application No. PCT/US2011/022650, 10 pages.

International Search Report and Written Opinion, mailing date Mar. 25, 2011, for International Application No. PCT/US2011/022651, 14 pages.

Silicon Labs Si1120, "QuickSense™ Si1120 Proximity and Ambient Light Sensor ICs", http://www.silabs.com/products/sensors/infraredsensors/Pages/Si1120.aspx [retrieved Dec. 28, 2010].

Sharp Electronics Corporation, "GP2Y0A02YK0F Sales and Technical Information", http://www.sharpmeg.com/Page.aspx/americas/en/part/GP2Y0A02YK0F/ [retrieved Dec. 28, 2010].

Theodore D. Rees, "Long Range Proximity and/or Motion Detector With Ambient Light Detection Capabilities", U.S. Appl. No. 61/173,951, filed Apr. 29, 2009.

David Stoppa et al. "An 80x60 Range Image Sensor Based on 10μm 50MHz Lock-In Pixels in 0.18μm CMOS", ISSCC 2010 / Session 22 / Image Sensors / 22.7, 2010 IEEE International Solid-State Circuits Conference.

Capella Microsystems, Inc. "Proximity Sensor", http://www.capellamicro.com.tw/EN/products_list.php?mode=16copyright 2009 [retrieved Mar. 14, 2011].

Capella Microsystems, Inc. "Ambient Light Sensor (ALS)", http://www.capellamicro.com.tw/EN/products_list.php?mode=14 copyright 2009 [retrieved Mar. 14, 2011].

OPTEK Technology Inc. "Long Distance Reflective Switch OPB720A and OPB720B Series", http://www.optekinc.com/datasheets/opb720a-06z.pdf, Issue F.1, Jan. 2008.

Intersil, "Low Power Ambient Light and Proximity Sensor with Intelligent Interrupt and Sleep Modes", ISL29028, FN6780.1, Mar. 2, 2010.

Silicon Labs Si1120, "Proximity/Ambient Light Sensor With PWM Output", Rev. 1.0 Aug. 2010 Copyright 2010 by Silicon Laboratories.

Davidovic et al. "Range Finding Sensor in 90nm CMOS with Bridge Correlator Based Background Light Suppression", pp. 298-301, 978-14244-6664-1/10/ © 2010 IEEE.

Nemecek et al., "Distance Measurement Sensor With PIN-Photodiode and Bridge Circuit", IEEE Sensors Journal, vol. 6, No. 2, pp. 391-397, Apr. 2006.

Gokturk et al, "A Time of Flight Depth Sensor—System Description, Issues and Solutions", 2004 Conference on Computer Vision and Pattern Recognition Workshop (CVPRW'04) vol. 3, Washington, D.C., USA, Jun. 27-Jul. 2, 2004.

Dongmyung Lee et al., "An 8.5Gb/s CMOSOEIC with On-chip Photodiode for Short Distance Optical Communications", 2010 IEEE International Solid-State Circuits Conference, Solid-State Circuits Conference Digest of Technical Papers (ISSCC), 2010 IEEE International, pp. 362-363, Feb. 7-11, 2010.

Amendment dated Dec. 14, 2012, in Taiwanese Patent Appl. No. 100103041 filed Jan. 27, 2011.

* cited by examiner

DIRECT CURRENT (DC) CORRECTION CIRCUIT FOR A TIME OF FLIGHT (TOF) PHOTODIODE FRONT END

CROSS REFERENCE TO RELATED APPLICATIONS

This application claims priority to U.S. Provisional Patent Application Ser. No. 61/298,895, filed on Jan. 27, 2010, and entitled "ARCHITECTURE FOR A REFLECTION BASED LONG RANGE PROXIMITY AND MOTION DETECTOR HAVING AN INTEGRATED AMBIENT LIGHT SENSOR," the entirety of which is incorporated by reference herein. Further, this application is related to co-pending U.S. patent application Ser. No. 12/979,726, filed on Dec. 28, 2010, entitled "DISTANCE SENSING BY IQ DOMAIN DIFFERENTIATION OF TIME OF FLIGHT (TOF) MEASUREMENTS," co-pending U.S. patent application Ser. No. 13/013,199, filed on Jan. 25, 2011, entitled "PHOTODIODE FRONT END WITH IMPROVED POWER SUPPLY REJECTION RATIO (PSRR)", co-pending U.S. patent application Ser. No. 13/013,173, filed on Jan. 25, 2011, entitled "AUTOMATIC ZERO CALIBRATION TECHNIQUE FOR TIME OF FLIGHT (TOF) TRANSCEIVERS," co-pending U.S. patent application Ser. No. 13/013,640, filed on Jan. 25, 2011, entitled "SERIAL-CHAINING PROXIMITY SENSORS FOR GESTURE RECOGNITION", and co-pending U.S. patent application Ser. No. 13/013,676, filed on Jan. 25, 2011, entitled "GESTURE RECOGNITION WITH PRINCIPAL COMPONENT ANALYSIS." The entireties of each of the foregoing applications are incorporated herein by reference.

DETAILED DESCRIPTION

Figure 1:
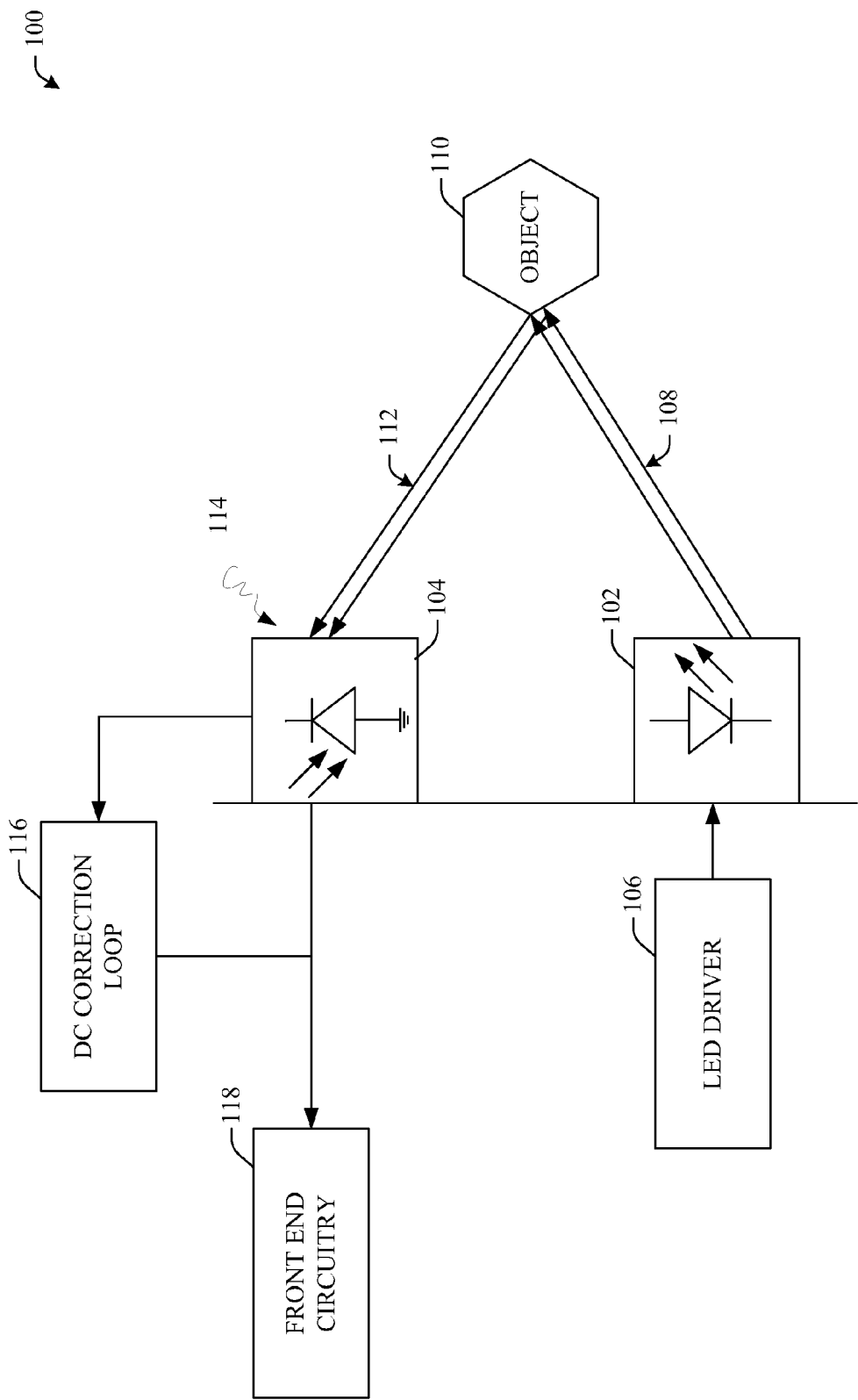
FIG. 1 illustrates an exemplary system for reducing direct current (DC) saturation in a front end of a long range proximity detector without introducing significant noise.

A category of monolithic devices is emerging that allows electronic products to sense their environment. These include diverse devices, such as, accelerometers, monolithic gyroscopes, light sensors and imagers. In particular, light sensors are one of the simplest and cheapest, allowing their inclusion in multitudes of consumer products, for example, nightlights, cameras, cell phones, laptops etc. Typically, light sensors can be employed in a wide variety of applications related to proximity sensing, such as, but not limited to, detecting the presence and/or distance of a user to the product for the purpose of controlling power, displays, or other interface options.

Infrared (IR) proximity detectors utilize IR light to detect objects within the sense area of the IR sensor. Moreover, IR light is transmitted by an IR Light emitting diode (LED) emitter, which reflects off of objects in the surrounding area and the reflections are sensed by a detector. Moreover, the detector can be a diode, e.g., a PIN diode, and/or any other type of apparatus that converts IR light into an electric signal. The sensed signal is analyzed to determine whether an object is present in the sense area. Some conventional systems transmit a pulse of IR light and detect whether the pulse is returned back at the pin diode. However, these conventional systems easily get confused by existing IR light in the world, e.g., ambient light, sunlight, etc. In addition, the conventional systems cannot differentiate between undesired reflections from static objects (e.g., chair, desk, soda can, etc.) and reflections from a desired object (e.g., a person, animal, etc.). Thus, to compensate for the existing IR light, the conventional systems measure the data twice; once when the IR transmitter is turned ON and an IR pulse is transmitted, and once when the IR transmitter is turned OFF. Moreover, the IR response is measured in the two cases and subtracted. However, performing these calculations is a tedious and time consuming process. Additionally, the range of such conventional detectors is only about 10-30 centimeters (cm). Further, to overcome the effects of the ambient light in a higher range, for example, range of 20-30 cm, a high amount of power needs to be transmitted by the IR LED.

The systems and methods disclosed herein provide a novel signal processing scheme for an active long-range distance sensor that prevents direct current (DC) saturation of the front end without contributing significant noise (e.g., noise spectral density). As an example, the range of the disclosed distance sensor can be 1-2 meters. In one aspect, the light emitted by an IR LED is modulated at a high frequency, for example 1 MHz-50 MHz. The received IR response is then demodulated, for example, by employing Quadrature amplitude demodulator (I/Q demodulation) and processed to identify the distance of an object from the sensor. It can be appreciated that although the subject specification is described with respect to IR light, the systems and methods disclosed herein can utilize most any wavelength. As an example, the subject system and/or methodology can be employed for acoustical proximity detection and/or ultrasonic range finding applications. Further, although the subject specification illustrates and describes light/optical sensors (e.g., photodiodes), it can be appreciated that most any circuit element that converts a physical input into an electrical signal.

The subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the subject matter may be practiced without these specific details. In other instances, well-known structures and devices are shown in block diagram form in order to facilitate describing the subject innovation. Of course, those skilled in the art will recognize that many modifications may be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. Further, the terms "sense area," "vision field," "optical field," and similar terminology are utilized interchangeably in the subject application, unless context warrants particular distinction(s) among the terms. Further, the term "ambient" employed herein can refer to light of most any reasonable spectrum, such as, but not limited to, incandescent light, fluorescent light, sunlight, any black-body temperature, and/or a combination thereof. Moreover, the term "ambient light" as employed herein can include most any light from a constant light source.

Referring to FIG. 1, there illustrated is an example system 100 for reducing DC saturation in a front end of a long range proximity detector, in accordance with an aspect of the subject disclosure. In general, system 100 can be employed in most any light sensing and/or optical proximity application. For example, a laptop or personal computer can power-up (e.g., from hibernation, stand-by, etc.) on detecting that a user has entered a room or a machine can alert an operator if the operator is at risk, when the operator is too close to the machine, by employing system 100. In another example, a cell phone or personal digital assistant (PDA) can switch off a display (to conserve battery life) when detected that the phone/PDA is held at the user's ear, by utilizing system 100.

Typically, system 100 employs Time-of-Flight (TOF) measurements, which rely on the finite speed of light. The finite speed causes a delay between the projection of an electromagnetic wave and its reflection from an object, which is proportional to the distance of the object. In system 100, the distance can be measured as a phase delay of a modulated (e.g., at 5 MHz) IR LED signal. Moreover, for proximity sensing based upon IR signal detection, system 100 employs an IR LED 102 and an IR sensor 104. For example, the system 100 can employ a high frequency (e.g., 5 MHz) modulated LED 102 and a tuned PIN detector 104 to optimize the detection range. Typically, a LED driver 106 can be employed to provide an input signal to the LED 102 (e.g., frequency modulated signal). Typically, a local oscillator (not shown) synchronous with the LED driver can be utilized for synchronous detection (e.g., by the sensor front end circuitry 118). As an example, the IR LED 102 has a typical peak wavelength that matches the proximity sensor spectrum, a narrow viewing angle with higher radiant intensity that can facilitate concentrating the energy that is ideal for proximity sensing. It can be appreciated that most any IR LED (or array) can be employed based on the factors, such as, but not limited to, view-angle, mechanic height, footprint, radiant intensity, current consumption, etc. Further, the IR LED 102 can emit the modulated IR signal 108 to the sensing object 110, and the IR sensor 104 can receive at least a portion 112 of the transmitted signal, which is reflected back from the surface of sensing object 110. The object 110 can be most any entity of interest, such as, but not limited to, a human entity, an automated component, a device, an item, an animal, etc.

Typically, the magnitude of the reflections 112 depends on the size of the object 110, the color of the object 110 and the distance of the object 110 from the IR sensor 104. As an example, a white shirt can produce higher reflections than a black shirt. In addition to the reflections 112 from the object 110, the sensor 104 can receive various other signals 114, such as, but not limited to, electrical crosstalk, optical crosstalk and/or environmental backscatter. Each of these signals represents interference to the detection of the object of interest. Of these interferences, electrical and optical crosstalk can be approximated to be relatively constant through the life time of the device, and can be calibrated at the manufacturing or development stage of the application. Environmental backscatter 114 can be received from various sources in the optical field of the sensor 104, and can include most any signal that is not of interest to the detection of the object 110. For example, objects such as a desk surface, a couch, a television display, a soda can, etc., are not useful targets, but are detected as a significant component of the signal received at the sensor 104. In one embodiment, these constant light sources (e.g., florescent lamps, sunlight, etc.) collectively contribute to ambient light incident on the sensor 104.

If a high amount of ambient light is received, the DC value of the current generated by the sensor 104 can increase and can lead to saturation of the front end circuitry 118. In one example, the "front end" as disclosed herein, can include amplifier(s), filter(s), demodulator, most any analog and/or digital signal processing circuits, and/or most any circuits that conform, the signal generated by the sensor to a specification, a back end can use. For example, the front end can include one or more amplifiers, one or more Analog-to-Digital converters (ADC), and/or a signal processor. In one aspect, system 100 utilizes DC correction loop 116 that adaptively adjusts thermal noise for different ambient light conditions and eliminates the DC saturation current introduced by the ambient light, without contributing significant noise (e.g., thermal noise, noise/$\sqrt{\text{frequency}}$) in system 100. In one example, the DC correction loop 116 can emulate an inductor that corrects the error signal created by ambient light as explained in detail infra with respect to FIGS. 2, 3, and 4.

It can be appreciated that the mechanical design of system 100 can include different component selections, component placement, dimensions, glass cover characteristics, LED selections, isolation techniques between sensor 104 and LED 102, etc., to achieve an optimal proximity sensing. Moreover, LED 102 can be most any light source, such as, but not limited to an LED, an organic LED (OLED), a bulk-emitting LED, a surface-emitting LED, a vertical-cavity surface-emitting laser (VCSEL), a super luminescent light emitting diode (SLED), a laser diode, a pixel diode, or the like. It can be appreciated that the light source can produce IR light, or light of most any other wavelength. Additionally, it can be appreciated that the sensor 104 can include most any light detecting elements, such as, but not limited to, a photo resistor, photovoltaic cell, photodiode, phototransistor, charge-coupled device (CCD), or the like, that can be used to produce a current or voltage indicative of the magnitude of detected light.

Further, it can be appreciated that the LED driver 106 and the front end circuitry 118 can include most any electrical circuit(s) that can include components and circuitry elements of any suitable value in order to implement the embodiments of the subject innovation. Furthermore, the LED driver 106, DC correction loop 116, and front end circuitry 118, can be implemented on one or more integrated circuit (IC) chips and can be included within the same or different package(s). Typically, various IR bands can be employed in imaging systems (e.g., Near IR, Mid-Wave IR and Long-Wave IR). Each band can have unique LEDs and Sensors. Oftentimes, some visible detector systems can work in the Near IR band and can include the detector integrated into the system IC. In addition, it can be appreciated that system 100 is not limited to utilizing IR light, and LEDs/sensors/detectors can utilize signals of most any wavelength.

Figure 2:
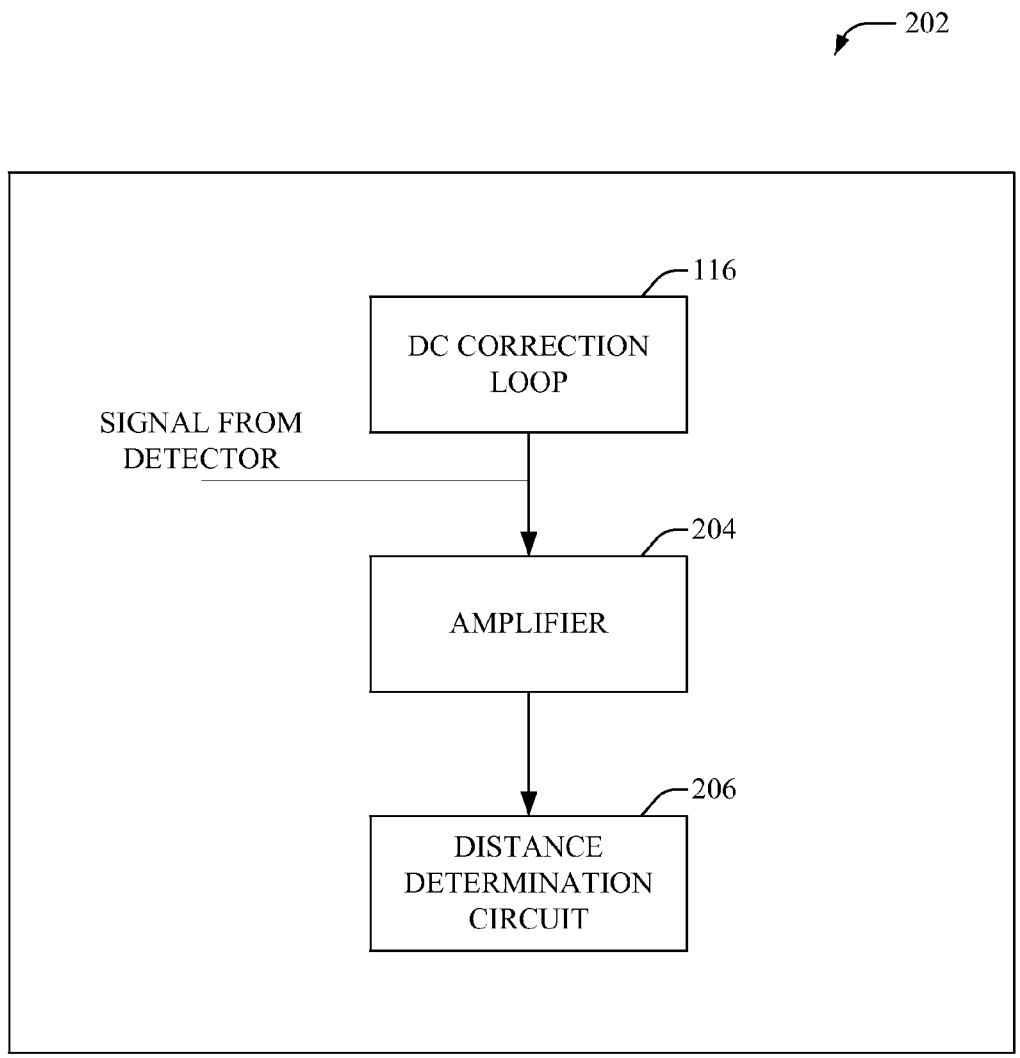
FIG. 2 illustrates an exemplary system that includes an Integrated Circuit (IC) chip, which corrects an error signal generated by an optical sensor due to ambient light, during distance sensing.

Referring now to FIG. 2, there illustrated an example system that includes an IC 202, which corrects an error signal, generated by a sensor due to ambient light, during distance sensing, according to an aspect of the subject specification. Moreover, IC 202 can be employed as a primary distance monitoring system and/or as a means to calibrate a traditional system. Specifically, IC 202 includes a DC correction loop 116, an amplifier 204, and a distance determination circuit 206, that identifies the distance of an object from the PIN diode. It can be appreciated that the DC correction loop 116 can include functionality, as more fully described herein, for example, with regard to system 100. Further, although a single IC (202) is illustrated in FIG. 2, it can be appreciated that multiple ICs or apparatus can be employed to implement the subject system.

The active IR proximity detector, disclosed herein, employs an IR LED emitter to transmit IR light, which reflects off of objects in the sense area and the reflections from the objects are sensed by a detector, e.g., a pin diode. Typically, along with the reflected light, ambient light is also incident on the detector. In particular, the ambient light and/or other error signals (e.g., leakage current from the photodiode) contribute to a DC value to the current generated by the detector. As an example, ambient light can include most any low frequency light including sunlight, artificially generated light (e.g., intended to light a room or an area), and/or shadows/light from moving objects that may not be of interest. In another example, the ambient light can also include higher frequency variations from manmade sources such as 100 Hz or 120 Hz light with various higher harmonics from lights driven directly from the power lines. The ambient light may also include even higher frequencies from florescent lighting driven with small transformer circuits in the 100 KHz frequency range and those harmonics. Traditionally, gain switching systems, wherein the system gain is adaptively changed to respond to ambient light can be utilized to correct the DC error caused by the ambient light. Alternately, a switched capacitor cancellation technique or a Transimpedance Amplifier (TIA) with a DC feedback loop can be utilized for DC correction. However, these complex systems can introduce significant noise (e.g., noise spectral density) at the front end of the detector. In contrast, DC correction loop 116 employs a simplistic, robust and low noise circuit that can enables the detector front end to maintain constant gain, thus simplifying design.

In one aspect, the DC correction loop 116 allows for the entire range of DC current (e.g., generated due to ambient light and/or most any error signal), to be accommodated with an insignificant noise penalty at the modulation frequency (e.g., 5 MHz). Moreover, the DC correction loop 116 provides a circuit that passes the high frequency light signal (e.g., reflected from an object) to an amplifier 204 or filter (not shown) while eliminating/reducing the lower frequency signal generated by ambient light incident on the detector. In an example, the DC correction loop 116 emulates an inductor that removes the DC component from the diode current and prevents saturation of the front end of the proximity detection circuit. In particular, the architecture utilized by the DC correction loop 116 enables DC correction without adding thermal noise (e.g. low noise spectral density) at the modulation frequency. Example circuits employed for the DC correction loop are described in detail with respect to FIGS. 3 and 4. The DC correction loop 116 can typically include two amplifiers, for example, transconductance amplifiers ($gm_1$ and $gm_2$). In addition, a capacitor resistor pair ($C_F$, $R_F$), can be utilized to attenuate the noise transfer function of the first transconductance amplifier ($gm_1$), while the bias of the second transconductance amplifier ($gm_2$) is automatically and dynamically adjusted to reduce noise.

The high frequency signal from the DC correction loop is then passed to one or more font end amplifiers 204. The amplified signal is provided to a distance determination circuit 206 employed for proximity/motion detection. In one example, the distance determination circuit 206 can include a demodulator, for example, a demodulation circuit that demodulates the amplified signal, and a circuit that identifies the phase of the demodulated signal for TOF measurements.

Figure 3:
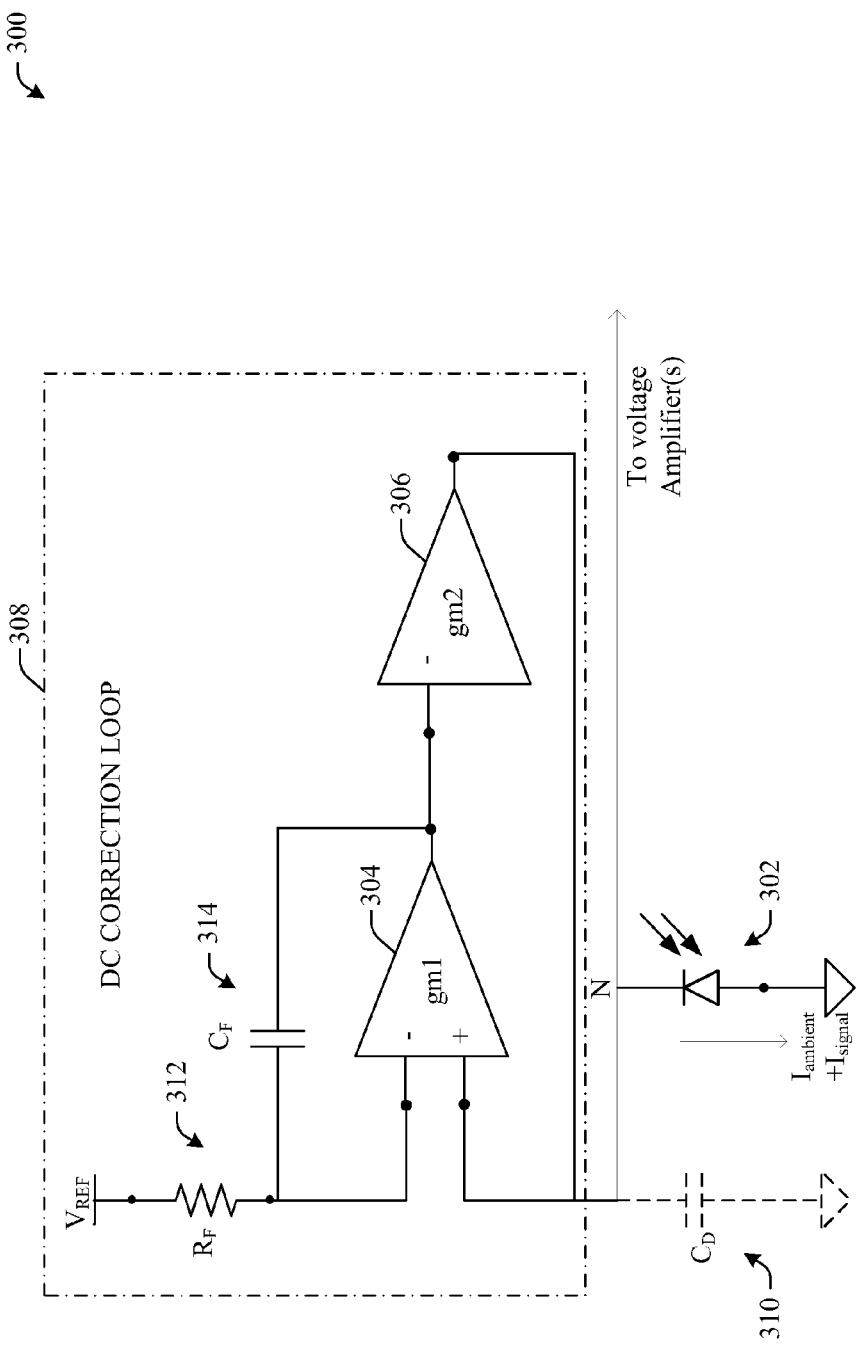
FIG. 3 illustrates an exemplary circuit diagram that compensates for the direct current (DC) current generated by an optical sensor.

FIG. 3 illustrates an example circuit diagram 300 that compensates for the DC current generated by an optical sensor in accordance with an aspect of the subject innovation. In one example, the circuit 300 enables a TOF front end to operate in the presence of ambient light (e.g., up to 100 klux) without saturation. Additionally, the circuit 300 does not add significant noise (e.g. noise power spectral density) to the front end at the modulation frequency. Moreover, the terms "significant noise" and/or "substantial noise" as used herein, refer to a value of noise power spectral density above a predefined threshold at which an error will be introduced in the proximity and/or motion detection.

Photodiode 302 generates a current $I_{ambient+signal}$ in response to the light incident on it and provides a capacitance $C_D$ 310. The light incident on the photodiode 302 include light reflected from an object (contributes to $I_{signal}$) and undesired ambient light (contributes to $I_{ambient}$). The part of the current generated by the photodiode 302 due to ambient light introduces a DC component in the diode current. Typically, the DC component can cause an error which can risk saturating the detector front end. In one aspect, the DC correction loop 308, provided in parallel with the photodiode 302, emulates an inductor, and thus swallows the DC component of the diode current that is generated due to ambient light. Moreover, the DC correction loop 308 allows the DC component to be corrected without adding significant thermal noise at the modulation frequency (e.g., 5 MHz).

The DC correction loop 308 includes amplifiers gm1 (304) and gm2 (306) and a capacitor resistor ($C_F$, $R_F$) pair connected at the inverting terminal of gm1 (304). Specifically, $C_F$ $R_F$ attenuates the noise transfer function of gm1 (304). The reference voltage $V_{REF}$ (e.g., ground) connection on resistor $R_F$ establishes the DC bias point for the photodiode 302, which is an important factor for the operation of a PIN photodiode. In addition, gm2 is adaptively changed by adjusting its bias, to adjust/control/reduce noise spectral density. Moreover, gm2 (306) adapts to changes in ambient current, such that, the noise contribution of the DC correction loop 308 is kept well below the noise contribution of the ambient light itself. Specifically, as the value of ambient current changes, the value of gm2 is changed, based on the bias applied by the output of gm1, to ensure that the noise level of circuit 300 is not significant.

In one aspect, the DC correction loop 308 ideally brings the DC transfer function at the photodiode node (N) to zero and no DC component passes through the rest of the circuitry, for example, voltage amplifier(s), filter(s), etc. Moreover, since the DC correction loop 308 emulates/acts as an inductor, a short circuit to ground is provided for the DC component. Accordingly, the DC correction loop generates 308 a zero at DC and prohibits the DC component signal from entering the sensor front end (e.g., voltage amplifier(s)). The signal, output from circuit 300, can be provided to the voltage amplifier(s) and further for analog and/or digital signal processing that facilitate proximity/motion detection. Moreover, the output signal does not include the DC component caused by ambient light and thus protects the front end from saturation.

In addition, the loop gain for the DC correction loop 308 can be calculated as follows:

$$Loop\,gain = \frac{-gm2}{sC_D} \frac{(1 + sC_F R_F)}{sC_F R_F}$$

Wherein,
$C_F$ is the capacitance of capacitor $C_F$ 314;
$R_F$ is the resistance of resistor $R_F$ 312;
gm2 is the gain of amplifier gm2;
$C_D$ 310 is the capacitance of photodiode 302; and
s is a constant.

According to one embodiment, $R_F$ 312 can be implemented as a metal-oxide semiconductor (MOS) transistor that can track gm2 (306) over temperature. The MOS transistor enables more accurate frequency response control for the loop about the LED modulation frequency. The $R_F$ tracking technique is described in detail with respect to amplifier compensation in Brehmer et al., U.S. Pat. No. 4,458,212, entitled "COMPENSATED AMPLIFIER HAVING POLE ZERO TRACKING," which is incorporated by reference herein. Moreover, $R_F$ tracking of gm2 (302) can be employed for better control of the loop frequency response over temperature and process.

Figure 4:
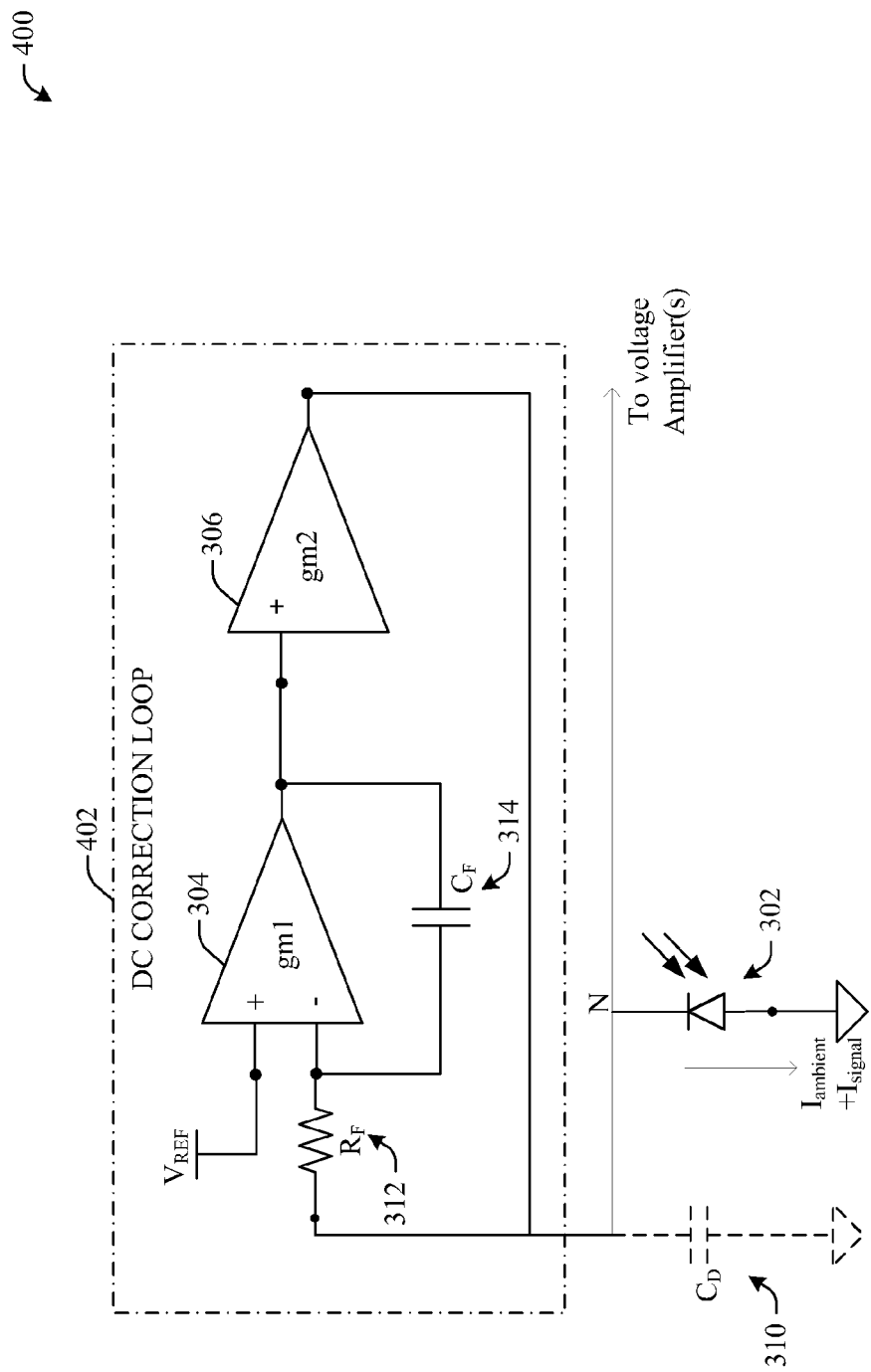
FIG. 4 illustrates an exemplary circuit for a low noise DC correction circuit utilized in time of flight (TOF) measurements in accordance with an aspect of the disclosed specification.

Referring to FIG. 4, there illustrated is another example circuit 400 for a low noise DC correction circuit utilized in TOF measurements in accordance with an aspect of the disclosed specification. Moreover, the DC correction loop 402 can control the signal to noise ratio (SNR) at a particular frequency, for example, modulation frequency (5 MHz) and reduce/remove the DC component in the diode current generated by photodiode 302 in response to ambient light.

Similar to DC correction loop 308, the DC correction loop 402 can be provided in parallel to the photodiode 302, to compensate for the diode current generated by ambient light incident on the photodiode 302. Moreover, the DC correction loop 402 emulates/acts as an inductor and thus provides a path for the DC component to ground. In particular, the DC correction loop 402 generates a zero at DC and prohibits the DC component signal from entering the sensor front end (e.g., voltage amplifier(s)). As an example, a non-inverting input of a first amplifier gm1 (304) can be connected to a reference voltage ($V_{ref}$), for example, ground, while the inverting input can be connected to node N via resistor $R_F$ 312. Moreover, the $V_{ref}$ connection on the non-inverting input of amplifier gm1 (304) establishes the DC bias point for the photodiode 302. Further, a capacitor $C_F$ 314 is included within a feedback loop of gm1 (304), such that, $C_F R_F$ attenuates the noise transfer function of gm1 (304). Additionally, the output of gm1 (304) is provided to the non-inverting input of gm2 (306) and is employed to control the bias of gm2 (306). Accordingly, as the value of ambient current changes, the value of gm2 (306) changes, such that, the noise introduced by the DC correction loop 402 is less than the noise introduced by the ambient current.

In one aspect, $R_F$ 312 can be implemented as a MOS transistor that provides better control of the loop frequency response over temperature and process. Specifically, the MOS transistor can track gm2 (306) over temperature and enable a more accurate frequency response control for the loop about the LED modulation frequency. The $R_F$ tracking technique is described in detail with respect to amplifier compensation in Brehmer et al. (U.S. Pat. No. 4,458,212), which is incorporated by reference herein.

Figure 5:
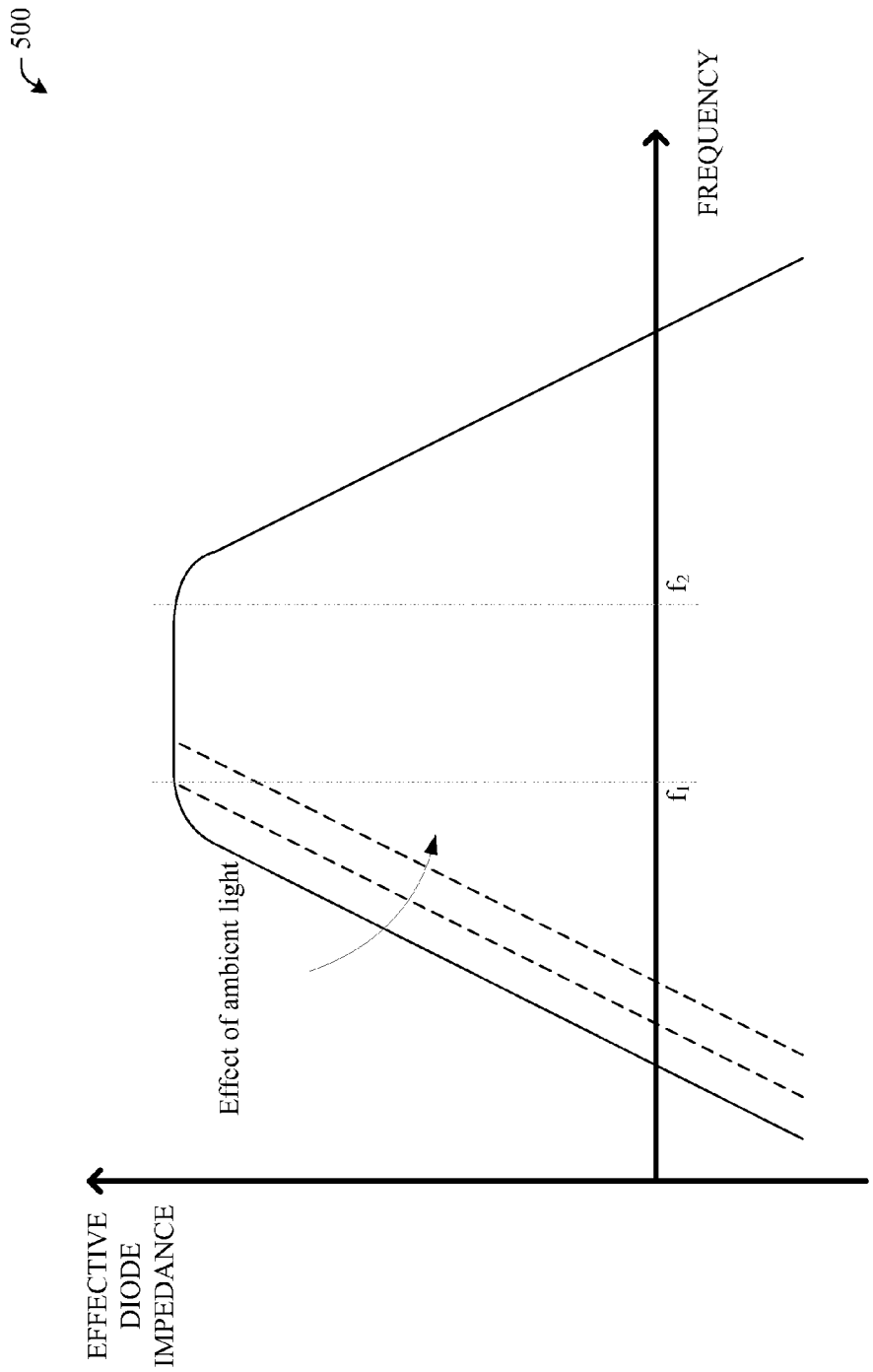
FIG. 5 illustrates an exemplary frequency domain plot for effective photodiode impedance, according to an aspect of the subject disclosure.

FIG. 5 illustrates an example frequency domain plot 500 for effective photodiode impedance, according to an aspect of the subject disclosure. Photodiode 302, in circuit 300 and/or 400, can convert incident light to current. The effective impedance, $|Z_{diode}|$, of the photodiode vs. frequency is illustrated in FIG. 5. Moreover, the effective impedance, $|Z_{diode}|$, can be calculated as follows:

$$\frac{Vin}{Iin} = \frac{\frac{sC_F R_F}{gm2}}{\frac{s^2 C_F R_F C_D}{gm2} + sC_F R_F + 1}$$

Wherein,
Vin is the input voltage;
Iin is the input current;
$C_F$ is the capacitance of capacitor $C_F$ 314;
$R_F$ is the resistance of resistor $R_F$ 312;
gm2 is the gain of amplifier gm2;
$C_D$ 310 is the capacitance of photodiode 302; and
s is a constant.

As seen in plot 500, for very low frequency, the effective impedance, $|Z_{diode}|$, of the photodiode is zero. In other words, at low frequencies, no voltage will be generated at node N. Further, the effect of ambient light can be seen from the characteristics of the frequency response of the DC correction loop (308 and/or 402). Moreover, the impedance represents the gain, which is ideally zero at DC (which indicates that DC is completely removed by the DC correction loop 308 and/or 402). Initially, the gain increases with increase in frequency and at the desired frequency the gain is significantly higher than the DC. Further, at a certain frequencies ($f_1$ to $f_2$) the frequency response plateaus and then rolls off again (at $f_2$). Typically, if the wanted signal (e.g., signal generated in response to light reflected from the object) is provided within the plateau frequency range, it will pass normally. In other words the factor of attenuation between the wanted signal and DC is very significant between $f_1$ and $f_2$.

Figure 6:
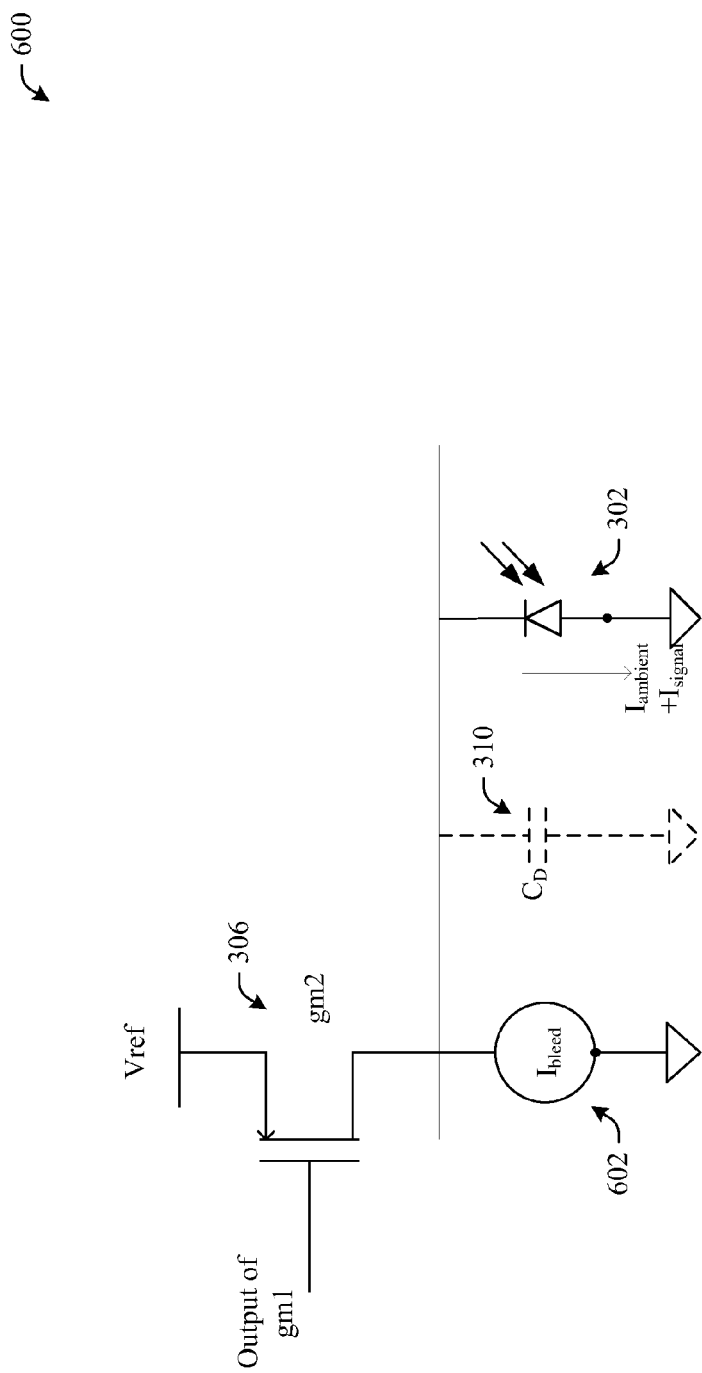
FIG. 6 illustrates an exemplary circuit that implements a p-channel metal-oxide-semiconductor (PMOS) device within the DC correction loop for DC attenuation.

Referring now to FIG. 6, there illustrated is example circuit 600 that implements a PMOS (p-channel metal-oxide-semiconductor) device within the DC correction loop for DC attenuation, according to an aspect of the subject innovation. According to an embodiment, gm2 (306) can be implemented as most any PMOS device, such as, but not limited to PMOS transistor 306. The bias of PMOS transistor 306 is controlled by the output of gm1, as shown in FIGS. 3 and 4. The noise introduced by the DC correction loop is dominated by the value of gm2 (gain of PMOS transistor 306). Accordingly, if value of gm2 increases, the power spectral density noise generated by the DC correction loop increases. By adaptively changing the value of gm2, the DC correction loop ensures that the noise due to the PMOS transistor 306 is substantially less than the noise introduced by the ambient current.

Moreover, the bias of the PMOS transistor 306 is adaptively changed based on the ambient light signal, to adaptively change the value of gm2, such that, the noise contributed by the PMOS transistor 306 is substantially less than the noise contributed by the ambient signal. Further, as current source $I_{bleed}$ 602 decreases, low noise is introduced at low ambient signal whereas when ambient signal increases, shot noise dominates. However, the noise introduced by the DC correction loop is always less than that introduced by the ambient current. In an aspect, the PMOS transistor 306 can include a more complex circuit element (e.g., a complex amplifier) than a single field effect transistor (FET), such that the conductance of the complex element can be controlled and size can be switched.

Output current is controlled by the PMOS transistor 306, which in turn is controlled by the amplifier gm1. Moreover, amplifier gm1, compares the reference voltage (e.g., ground) with the feedback voltage from the output and amplifies the difference. If the feedback voltage is lower than the reference voltage, the gate of the PMOS device is pulled lower, allowing more current to pass and increasing the output voltage. If the feedback voltage is higher than the reference voltage, the gate of the PMOS device is pulled higher, allowing less current to pass and decreasing the output voltage.

Figure 7:
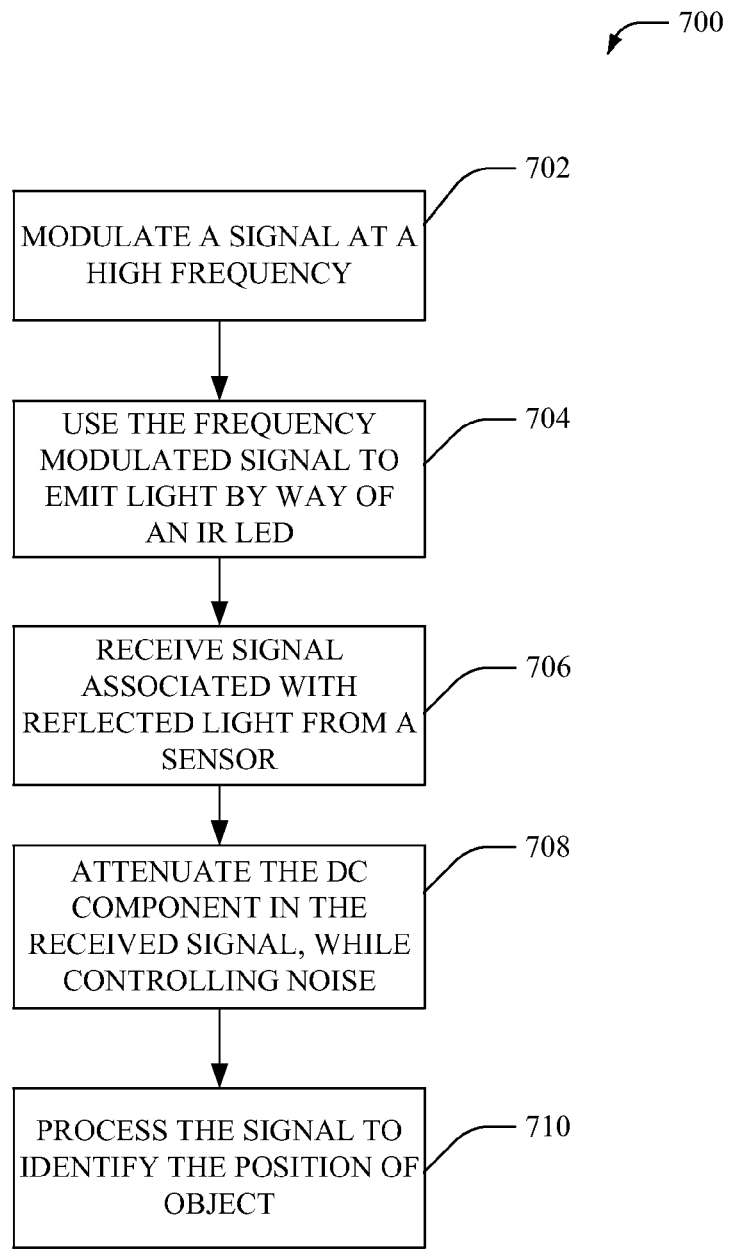
FIG. 7 illustrates an exemplary methodology that can discern distance of an object or distance at which motion occurred, while ignoring the effects of ambient light incident on a sensor.

FIG. 7 illustrates a methodology and/or flow diagram in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or computer-readable storage/communications media.

FIG. 7 illustrates an example methodology 700 that can discern distance of an object or a distance at which motion occurred, while ignoring the effect of ambient light incident on a sensor. Typically, methodology 700 can be utilized in various applications, such as, but not limited to consumer electronic devices (e.g., cell phones, laptops, media players, gaming systems, night-vision systems, etc.), mechanical systems (e.g., door/window mechanism), industrial automation systems, robotics, etc.

At 702, a signal, for example, input to an emitter (e.g., IR LED), can be modulated at a high frequency in the Megahertz range (e.g., 1 MHz-50 MHz). As an example, most any modulation technique can be employed for modulation. At 704, the frequency modulated signal can be utilized by the IR LED to emit light. Typically, the range of the IR LED can be selected based on the application (e.g., 1-2 meters). The emitted IR signal is reflected back from object(s) (moving and/or stationary) within the optical field and the reflected signals can be received at an optical sensor, for example, an IR sensor, along with ambient light (e.g., sunlight, florescent lights, lamps, bulbs, etc.). At 706, the signal is received from the sensor and at 708 the DC component in the received signal, for example, generated due to the ambient light incident on the sensor, can be attenuated, while controlling the noise contributed by the attenuation circuit. Further, at 710 the signal can be processed, for example, amplified, filtered, demodulated, etc. to identify the position of the object(s) and/or position at which motion occurred. Typically, the signal can be amplified by employing one or more amplifiers and demodulated by employing a Quadrature Amplitude demodulator. Moreover, phase data can be identified based on the demodulation, which in turn can be utilized to identify proximity or motion of an object.

Figure 8:
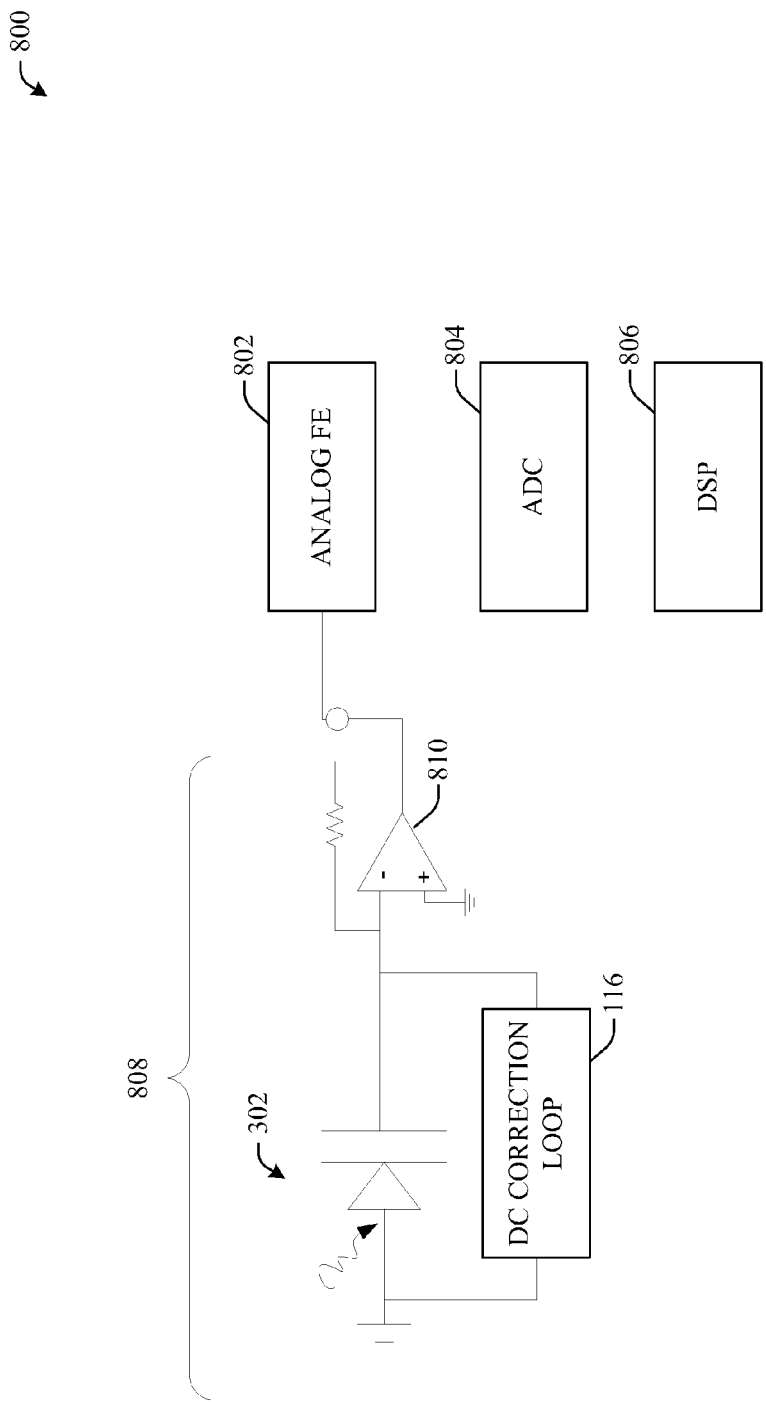
FIG. 8 illustrates an exemplary functional block diagram for the architecture of the subject innovation.

In order to provide additional context for various aspects of the subject specification, FIG. 8 illustrates an exemplary functional block diagram for the architecture 800 of the subject innovation. In one aspect, the systems (e.g., illustrated in FIGS. 1-4 and 6) disclosed herein can be employed in a reflection based proximity and motion detector with or without an integrated ambient light sensor (ALS). The architecture 800 includes a LED and associated driver circuitry (not shown for simplicity), a photodiode sensor 302, an analog front end and signal processing 802, data conversion circuitry (e.g., analog-to-digital converter 804), digital control and signal processing 806 (e.g., complex programmable logic device (CPLD), interface circuitry (not shown for simplicity) and/or results display (not shown for simplicity). The architecture 800 adaptively optimizes sensitivity and power for a given environment. Moreover, the architecture 800 derives significant performance improvements and reduces the risk of front end saturation.

According to an aspect of the subject innovation, the architecture 800 includes a Front End (FE), which includes a Trans-Inductance Amplifier (TIA). As an example, DC corrections circuits 300, 400, and 600, disclosed supra, can be implemented within DC correction loop 116 of section 808. Moreover, the DC correction loop 116 attenuates a DC component (e.g., error signal) of the electrical signal generated by the detector. Further, the DC correction loop 116 contributes less noise than that contributed by one or more signal processing components in a front end (e.g., amplifier 810, analog FE 802, ADC 804, etc.) of the reflection based proximity detector.

Typically, the output of the Front End 808 can be subjected to multiple stages of voltage gain to maximize the SNR of the output signal. For example, the voltage gain is adaptively set based on the magnitude of the signal received from the Front End 808, which includes the desired signal to be measured. The interferers are dynamically calibrated out of the measurement to improve the sensitivity (e.g., by the DC correction loop 116). The architecture 800 can also include a Demodulator (not shown for simplicity) with low pass filters (LPFs) that perform frequency demodulation, Converters (ADCs) 804, a Universal Serial Bus (USB) processor for a Control Interface, and a Computer Programmable Logic Device (CPLD) that include several modules. Moreover, the digital signal processor (DSP) 806 can process the digital signal to identify proximity of an object, motion of an object and/or presence of an object within a sense field of the sensor 302.

The architecture 800 of the subject innovation can be used in many applications including computers, automotive, industrial, television displays and others. For example, the architecture 800 can be used to detect that a user has entered the room and automatically cause a laptop computer in hibernation mode to wake up and enter into the active mode so that the user can use it. According to an aspect of the subject innovation, the architecture 800 can perform motion and proximity sensing at a range of up to 1-2 meters. According to another aspect of the subject innovation, the architecture 800 of the subject innovation can perform its operations by using less than twenty milli-watts (mW) of power.

In one embodiment of the subject innovation, the entire architecture 800 can be implemented in a single integrated circuit chip (IC) along with the LED driver circuitry and the LED. In another embodiment of the subject innovation, all components of the architecture 800 can be implemented in the IC except for the LED driver circuitry and the LED, which can be implemented outside the IC. In yet another embodiment of the subject innovation, various components of the architecture 800 can be located inside or outside the IC.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

The aforementioned systems/circuits/modules have been described with respect to interaction between several components. It can be appreciated that such systems/circuits/modules and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art. Moreover, the components and circuitry elements described above can be of any suitable value in order to implement the embodiments of the subject invention. For example, the resistors can be of any suitable resistance, capacitors can be of any suitable capacitance, amplifiers can provide any suitable gain, etc.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A system, comprising:
   a driver configured to produce a high frequency (HF) drive signal that can be used to drive a light emitting element with the HF drive signal to thereby cause a HF light signal to be emitted;
   an optical sensor configured to produce a sensor signal indicative of light that is incident on the optical sensor,
      wherein the sensor signal includes a low frequency (LF) component and a HF component,
      wherein the LF component, which includes a direct current (DC) component, is indicative of ambient light that is not of interest, and
      wherein the HF component is indicative of reflected light that is of interest;
   front end circuitry including one or more amplifiers and/or one or more filters; and
   DC correction loop circuitry including a pair of transconductance amplifiers and configured to remove the LF component from the sensor signal, while passing the HF component of the sensor signal to the front end circuitry, to thereby prevent DC saturation of the front end circuitry.

2. The system of claim 1, wherein the DC correction loop circuitry comprises:
   a first transconductance amplifier (gm1) including a non-inverting (+) input, an inverting input (−) and an output;
   a second transconductance amplifier (gm2) including an input coupled to an output of the first transconductance amplifier (gm1) and an output coupled to the non-inverting (+) input of the first transconductance amplifier (gm1);
   a capacitor coupled between the output of the first transconductance amplifier (gm1) and the inverting (−) input of the first transconductance amplifier (gm1); and
   a resistor coupled between the inverting (−) input of the first transconductance amplifier (gm1) and a reference voltage (Vref);
   wherein the non-inverting (+) input of the first transconductance amplifier (gm1) and the output of the second transconductance amplifier (gm2) are coupled to a node that couples a terminal of the optical sensor to the front end circuitry.

3. The system of claim 2, wherein:
   the second transconductance amplifier (gm2) comprises a PMOS transistor including a gate, a source and a drain;
   the input of the second transconductance amplifier (gm2) comprises the gate of the PMOS transistor; and
   the output of the second transconductance amplifier (gm2) comprises the drain of the PMOS transistor.

4. The system of claim 1, wherein the DC correction loop circuitry comprises:
   a first transconductance amplifier (gm1) including a non-inverting (+) input, an inverting input (−) and an output;
   a second transconductance amplifier (gm2) including an input coupled to an output of the first transconductance amplifier (gm1) and an output;
   a capacitor coupled between the output of the first transconductance amplifier (gm1) and the inverting (−) input of the first transconductance amplifier (gm1);

a resistor that couples the output of the second transconductance amplifier (gm2) to the inverting (−) input of the first transconductance amplifier (gm1);

wherein the non-inverting (+) input of the first transconductance amplifier (gm1) is coupled to a reference voltage (Vref);

wherein the inverting (−) input of the first transconductance amplifier (gm1) is coupled by the resistor to a node that couples a terminal of the optical sensor to the front end circuitry; and wherein the output of the second transconductance amplifier (gm2) is coupled to the node that couples the terminal of the optical sensor to the front end circuitry.

5. The system of claim 4, wherein:

the second transconductance amplifier (gm2) comprises a PMOS transistor including a gate, a source and a drain;

the input of the second transconductance amplifier (gm2) comprises the gate of the PMOS transistor; and the output of the second transconductance amplifier (gm2) comprises the drain of the PMOS transistor.

6. The system of claim 1, wherein a frequency of the emitted HF light signal and a frequency of the HF component of the sensor signal are within a range of 1 MHz-50 MHz.

7. The system of claim 1, wherein:

the front end circuitry is coupled to a terminal of the optical sensor; and the DC correction circuitry is coupled to the terminal of the optical sensor that is coupled to the front end circuitry.

8. The system of claim 1, wherein the DC correction loop circuitry is connected in parallel with the optical sensor.

9. The system of claim 1, wherein the DC correction loop circuitry is configured to emulate an inductor without using an inductor.

10. The system of claim 1, wherein the DC correction loop circuitry does not include a switched capacitor circuit.

11. The system of claim 1, wherein the DC correction loop circuitry introduces less thermal noise at a frequency of the HF component of the sensor signal than is introduced by the front end circuitry.

12. The system of claim 1, further comprising:

detection circuitry configured to detect a distance, presence and/or motion of an object relative to the optical sensor based on an output of the front end circuitry.

13. A DC correction loop circuit, comprising:

a first transconductance amplifier (gm1) including a non-inverting (+) input, an inverting input (−) and an output; and a second transconductance amplifier (gm2) including an input coupled to an output of the first transconductance amplifier (gm1) and an output coupled to the non-inverting (+) input of the first transconductance amplifier (gm1);

a capacitor coupled between the output of the first transconductance amplifier (gm1) and the inverting (−) input of the first transconductance amplifier (gm1); and a resistor coupled between the inverting (−) input of the first transconductance amplifier (gm1) and a reference voltage (Vref).

14. The DC correction loop circuit of claim 13, wherein the non-inverting (+) input of the first transconductance amplifier (gm1) and the output of the second transconductance amplifier (gm2) are coupleable to a node that couples a terminal of an optical sensor to front end circuitry.

15. The DC correction loop circuit of claim 13, wherein when the non-inverting (+) input of the first transconductance amplifier (gm1) and the output of the second transconductance amplifier (gm2) are coupled to a node that couples a terminal of an optical sensor to front end circuitry, the DC correction circuit prevents DC saturation of the front end circuitry.

16. The DC correction loop circuit of claim 13, wherein when the non-inverting (+) input of the first transconductance amplifier (gm1) and the output of the second transconductance amplifier (gm2) are coupled to a node that couples a terminal of an optical sensor to front end circuitry, the DC correction circuit removes a LF component from a sensor signal produced by the optical sensor, while passing a HF component of the sensor signal to the front end circuitry, to thereby prevent DC saturation of the front end circuitry.

17. The DC correction loop circuit of claim 13, wherein the DC correction loop circuit emulates an inductor without including an inductor.

18. The DC correction loop of claim 13, wherein:

the second transconductance amplifier (gm2) comprises a PMOS transistor including a gate, a source and a drain;

the input of the second transconductance amplifier (gm2) comprises the gate of the PMOS transistor; and the output of the second transconductance amplifier (gm2) comprises the drain of the PMOS transistor.

* * * * *